United States Patent
Leatt et al.

(10) Patent No.: US 11,957,623 B2
(45) Date of Patent: Apr. 16, 2024

(54) PROTECTIVE EYEWEAR WITH TEAR OFF OR ROLL-OFF FUNCTION

(71) Applicant: LEATT CORPORATION, Santa Clarita, CA (US)

(72) Inventors: Christopher James Leatt, Durbanville (ZA); Pieter André Keevy, Durbanville (ZA); Dominic Hamel, Durbanville (ZA)

(73) Assignee: LEATT CORPORATION, Santa Clarita, CA (US)

( * ) Notice: Subject to any disclaimer, the term of this patent is extended or adjusted under 35 U.S.C. 154(b) by 176 days.

(21) Appl. No.: 17/296,361

(22) PCT Filed: Dec. 18, 2019

(86) PCT No.: PCT/IB2019/061001
§ 371 (c)(1),
(2) Date: May 24, 2021

(87) PCT Pub. No.: WO2020/128886
PCT Pub. Date: Jun. 25, 2020

(65) Prior Publication Data
US 2021/0393440 A1    Dec. 23, 2021

(30) Foreign Application Priority Data
Dec. 20, 2018    (GB) .................................... 1820871

(51) Int. Cl.
*A61F 9/02*    (2006.01)
(52) U.S. Cl.
CPC .................................... *A61F 9/025* (2013.01)

(58) Field of Classification Search
CPC ............. A61F 9/02; A61F 9/025; A61F 9/029
See application file for complete search history.

(56) References Cited

U.S. PATENT DOCUMENTS

| 5,809,580 A | 9/1998 | Arnette |
| 6,415,452 B1 | 7/2002 | Watanabe et al. |
| 2012/0328828 A1 | 12/2012 | Mcinturff |

(Continued)

OTHER PUBLICATIONS

International Search Report for PCT/IB2019/061001 dated Mar. 19, 2020.

(Continued)

*Primary Examiner* — F Griffin Hall
(74) *Attorney, Agent, or Firm* — Stephen J. Weyer, Esq.; Stites & Harbison, PLLC

(57) ABSTRACT

Protective eyewear such as goggles (12) are provided with a frame (14) lens (20) and a pair of tabs (30) protruding from a front (32) of the lens (20) at lateral positions, to receive tear off sheets. The frame (14) includes lateral attachment formations (28) that can engage complemental attachment formations (46) on removable roll holders (34,36). Each roll holder (34,36) includes an anchor formation (50) with a recess (54) in which one of the tabs (30) is receivable. The roll holders (34,36) can be fitted on the attachment formations (28) and tabs (30) to use a roll-off system, or can be removed to use a tear off system. The frame (14) preferably has pivoting outriggers (22) which include the attachment formations (28), so that the roll holders (34,36) are attached to the outriggers (22) and can pivot off the lens (20) with the outriggers (22).

9 Claims, 4 Drawing Sheets

(56) References Cited

U.S. PATENT DOCUMENTS

2014/0157496 A1* 6/2014 Ginther .................. A61F 9/029
2/439
2015/0328050 A1 11/2015 Sigismondo et al.
2019/0142639 A1* 5/2019 Durham .................... A61F 9/02
2/439

OTHER PUBLICATIONS

United Kingdom Intellectual Property Office Search Report for GB 1820871.0 dated Mar. 22, 2019.
Written Opinion of the International Searching Authority for PCT/IB2019/061001 dated Mar. 19, 2020.

* cited by examiner

PROTECTIVE EYEWEAR WITH TEAR OFF OR ROLL-OFF FUNCTION

FIELD OF THE INVENTION

This invention relates to protective eyewear such as goggles for use in activities such as off-road motorcycling, in which the wearer's eyes require protection, but protective eyewear is exposed to dirt.

BACKGROUND TO THE INVENTION

Participants in activities such as motocross require eyewear to protect their eyes against dirt, among other risks. However, the eyewear itself is also exposed to dirt which often needs to be removed to allow the wearer sufficiently clear vision.

Two systems have been developed for use with protective eyewear in the form of goggles, to remove dirt from time to time to clear the wearer's vision. One of the systems is known as the "tear off" system comprising separate transparent sheets that are removably attached to the goggles and extend over at least part of the goggles' lens. Dirt collects on the outermost sheet and when required, the wearer simply removes (or "tears off") the outermost sheet, along with the dirt. Multiple sheets can be used on top of one another to allow successive vision clearing actions, but an excessive number of sheets can affect vision adversely.

Another vision clearance system is known as the "roll-off" system and comprises a strip of transparent sheet material that extends across the goggles' lens between two reels, located at opposing lateral positions. The sheet material can be fed from one roll and can be taken up by the other roll and in use, when a length of the sheet material in the wearer's field of vision has collected dirt, the wearer can rotate one real to roll up the dirty sheet material, while pulling clear sheet material from the opposing roll, to cover the lens. The rolls are typically housed in roll holders or canisters, which can restrict the wearer's lateral vision a little and the strip of sheet material typically only covers part of the goggles' lens, but a substantial length of sheet material that can be used during a ride (e.g. during a race), allowing sufficient sheet material to clear the wearer's vision frequently.

Most goggles are either equipped to use a tear off system or a roll-off system, so if a wearer wants the option to select between the two vision clearing systems, he requires multiple goggles. Some goggles have been developed which allow both types of vision clearing systems to be used on the same goggles, but these goggles either require cumbersome interchange of substantial parts, to change the goggles between suitability to support different vision clearing systems, or the attachment of either the tear sheets or the roll-off canisters, is sub-optimal (i.e. either the tear off sheets or the roll-off canisters do not fit properly).

The present invention seeks to provide protective eyewear such as goggles which are easy to use with either a tear off system, or a roll-off system.

SUMMARY OF THE INVENTION

According to a first aspect of the present invention there is provided protective eyewear such as goggles comprising a frame and a lens, said eyewear further comprising:
 a pair of engagement features disposed at opposing lateral positions on a front surface of the lens, each of said engagement features protruding from the front of the lens and being shaped and dimensioned for receipt of tear off sheets; and
 a removable pair of roll holders;
 wherein the frame includes first attachment formations disposed at opposing lateral locations and each of the roll holders includes one or more second attachment formations that are complemental to one of the first attachment formations, and each roll holder includes an anchor formation defining a recess in which one of the engagement features is receivable.

The frame may include a pair of outriggers that are pivotally attached to the rest of the frame, the first attachment formations being disposed on each of the outriggers.

Each of the roll holders may include a body and the anchor formation of each roll holder may be releasable from its body.

Each anchor formation may be releasably attachable to one of the engagement features and at least part of the body of each roll holder may be receivable between the anchor formation and frame.

The protective eyewear may include an attachment assembly comprising the two anchor formations and at least one, but preferably two resilient tensile elements extending between the anchor formations. The resilient elements could be completely, or partly elastic.

BRIEF DESCRIPTION OF THE DRAWINGS

For a better understanding of the present invention, and to show how it may be carried into effect, the invention will now be described by way of non-limiting example, with reference to the accompanying drawings in which.

DETAILED DESCRIPTION OF THE DRAWINGS

Figure 1:
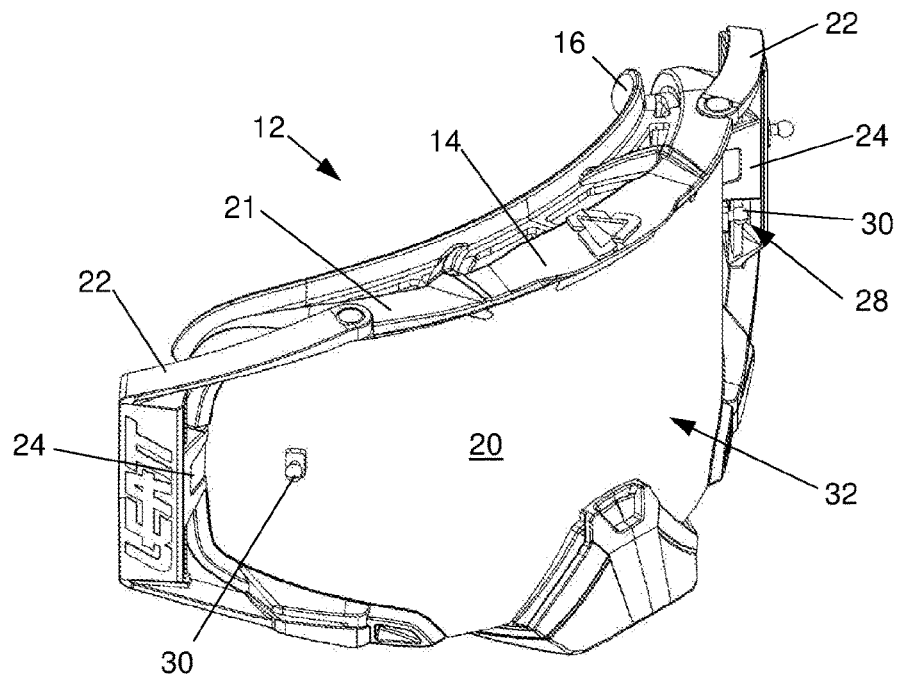
FIG. 1 shows an isometric view of goggles according to the present invention, without roll holders.

Referring to the drawings, protective eyewear in according to the present invention, in the form of goggles, are identified, generally, by reference sign 12.

Figure 2:
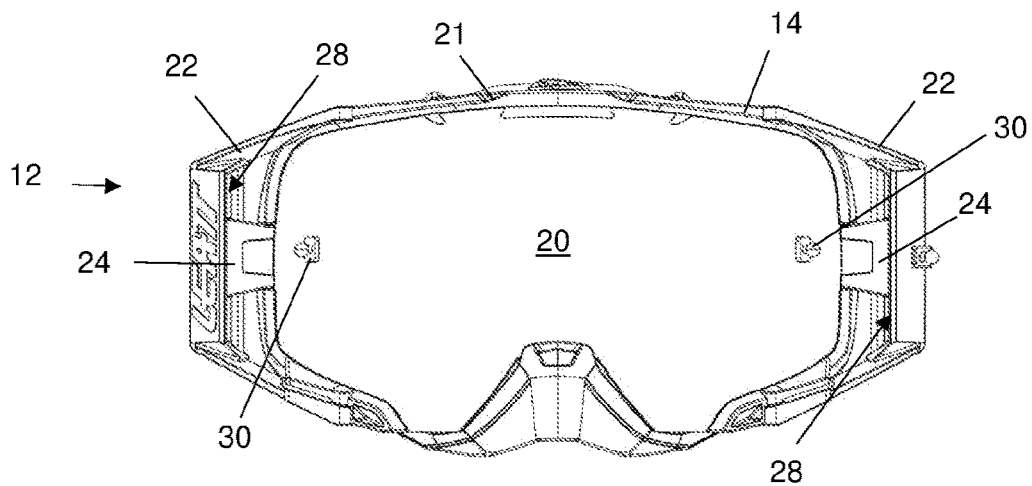
FIG. 2 shows a front view of the goggles of FIG. 1.
Figure 3:
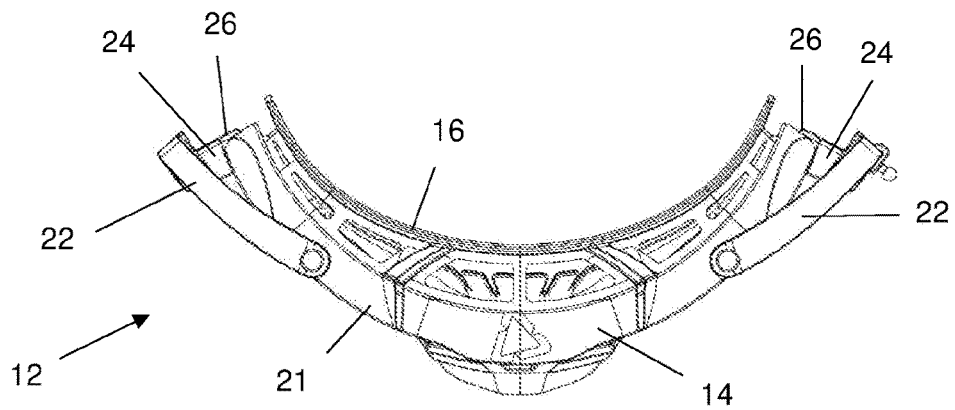
FIG. 3 shows a top view of the goggles of FIG. 1.
Figure 4:
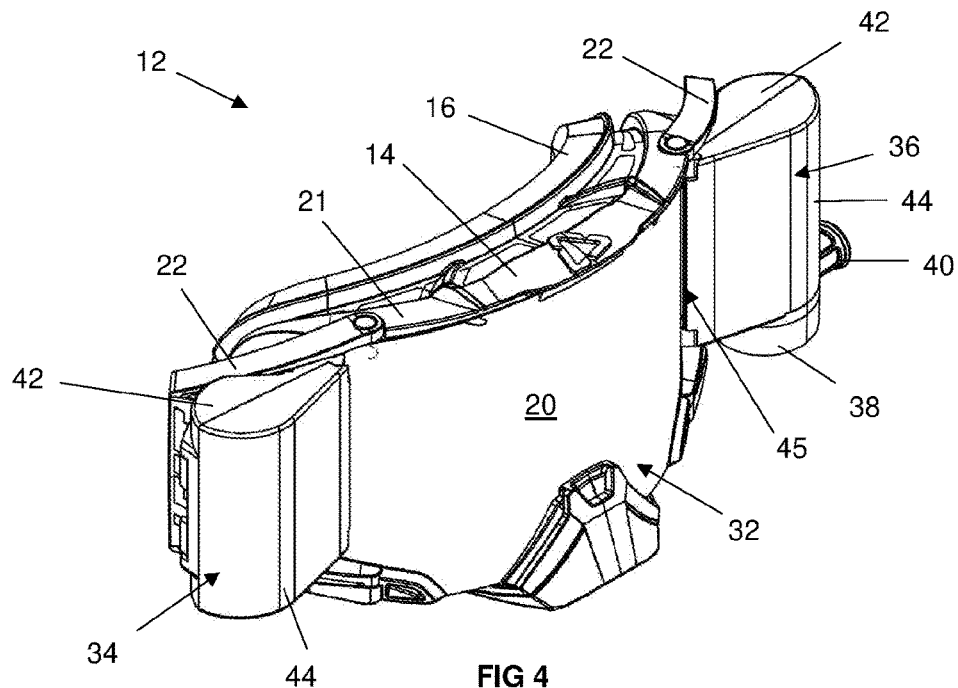
FIG. 4 shows an isometric view of the goggles of FIG. 1, with roll holders.
Figure 5:
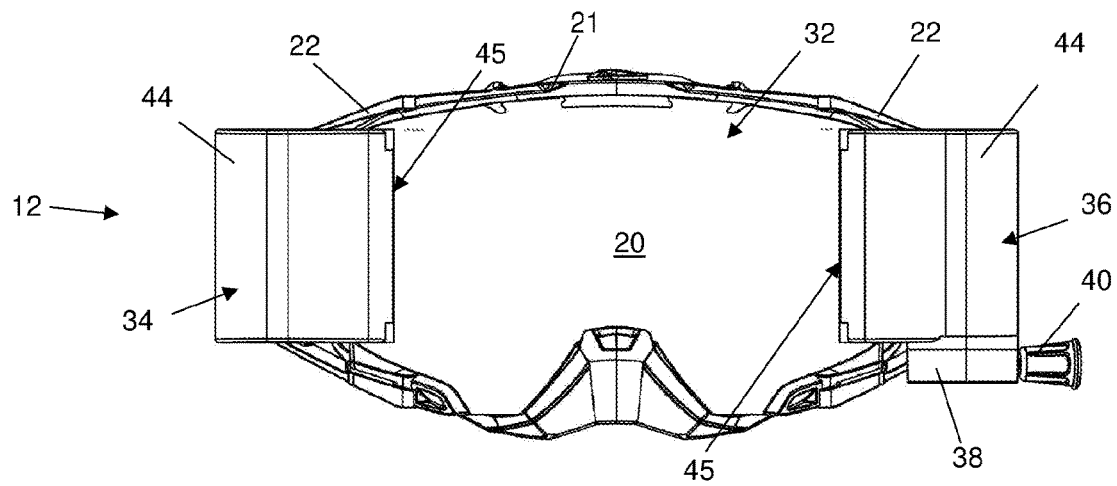
FIG. 5 shows a front view of the goggles of FIG. 4.
Figure 6:
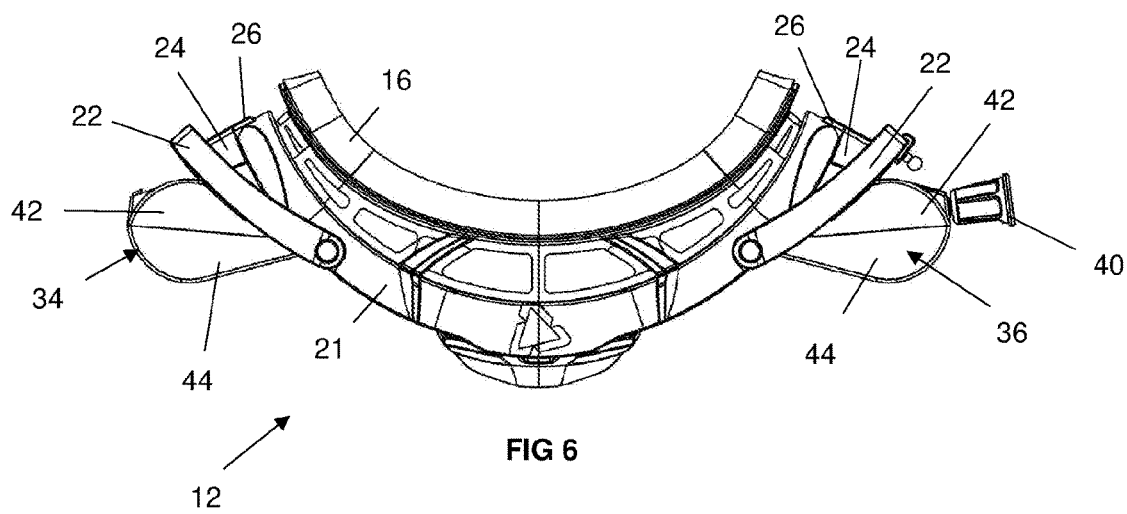
FIG. 6 shows a top view of the goggles of FIG. 4.

Referring to FIGS. 1-3, the goggles 12 include a frame 14 that is shaped to fit comfortably on a wearer's face and to extend around the wearer's field of vision, preferably with suitable padding 16 (which is shown incompletely in FIGS. 1-3, but is shown completely in FIGS. 4-6), if required. An elastic strap 18 (not shown in FIGS. 1-3, but shown in FIGS. 8 and 9) extends from lateral ends of the frame 14 and can extend around the sides and back of a wearer's head to keep the goggles 12 in position on the wearer's head.

The goggles 12 also include a lens 20 that is supported on the frame 14 and the lens is preferably curved. The lens 20 can be fixed in the frame 14, but is preferably removable to allow replacement. The frame 14 includes a frame body 21 and a pair of outriggers 22 that are preferably each pivotally attached to frame body and each outrigger has a lock formation 24 that preferably extends rearward from a lateral end of the outrigger. In the illustrated embodiment, each lock formation 24 is configured to hold a lateral edge of the lens 20 in position by pressing it against the frame body 21 and each lock formation includes a clip 26 for locking the outrigger relative to the frame body, however, other embodiments of the invention could have different means for holding the lens in position and/or may have different means for locking the outriggers relative to the frame body.

In other embodiments, the outriggers 22 may be fixedly attached to the frame body 21 or the frame 14 could itself be shaped to include the features of the outriggers described below, although a frame body with pivoting outriggers is preferred.

Each of the outriggers has first attachment formations in the form of recesses 28 that are disposed on lateral parts of the outriggers, the recesses being open towards the centre of the lens 20.

A pair of engagement features in the form of tabs 30 are provided on the lens 20 at lateral positions on the lens—which are preferably not at lateral ends of the lens, but are preferably spaced towards the periphery of the wearer's field of vision. The tabs 30 protrude from a front surface 32 of the lens 20 and are each shaped with a neck and rounded head, to receive transparent films or tear off sheets in the conventional manner.

In other embodiments, the goggles 12 could have differently shaped or configured engagement formations protruding from the front surface 32 of the lens 20 and/or could have differently shaped first attachment formations, however, the configurations of the tabs 30 and recesses 28 shown in the illustrated embodiment of the invention, are preferred for their compatibility with existing tear off and roll-off systems.

Referring to FIGS. 4-6 and 10, a pair of roll holders or canisters can be attached to the goggles 12, and the pair includes a feed roll holder 34 and a take-up roll holder 36. The feed roll holder 34 is configured to receive a reel of transparent film material inside and the take-up roll holder 36 is configured to receive a take-up reel inside, which is connected to a ratchetted drive mechanism 38, driven by pulling on a drawstring handle 40. The transparent film from the feed reel can pass over part of the front surface 32 of the lens 20 in the wearer's field of vision, and is rolled onto the take-up reel, in the conventional manner.

Each of the roll holders 34,36 includes a body 42 that is disposed at the rear of the roll holder and is attachable to the frame 14 and tabs 30. A cover 44 is attachable to the front of each body 42 in a clipping manner and a narrow slot 45 is defined between each body and its cover, on the side of the roll holder facing towards the centre of the lens 20, so that the transparent roll-off film can pass through the slot.

On the back of each body 42, there are second attachment formations in the form of a pair of tongues 46, which are complemental to the recesses 28 on the outriggers 22 and the tongues can be received in the recesses, preferably with a tight fit. In other embodiments of the invention, the shapes and configurations of the first and second attachment formations could be different, e.g. recesses could be provided on each body 42 and tongues on each outrigger 22.

Figure 10:
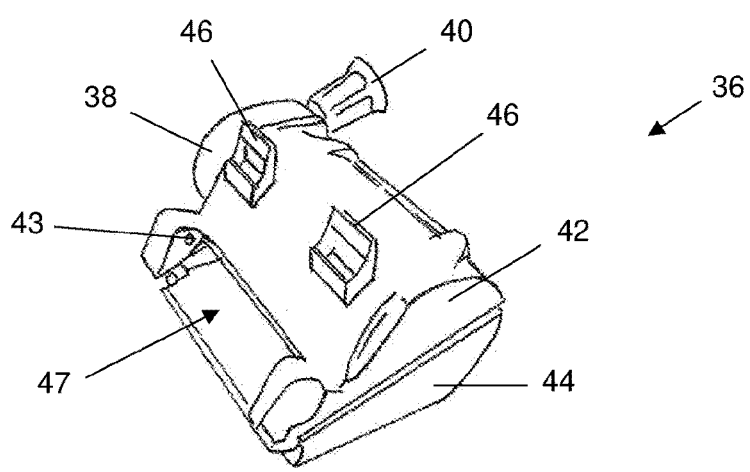
FIG. 10 shows a rear perspective view of a take-up roll holder according to the present invention.

As can be seen in FIG. 10, each roll holder body 42 defines a recess 47 and two clips 43 are each biased with a coil spring (not visible) and protrude from opposing sides into the recess.

Figure 7:
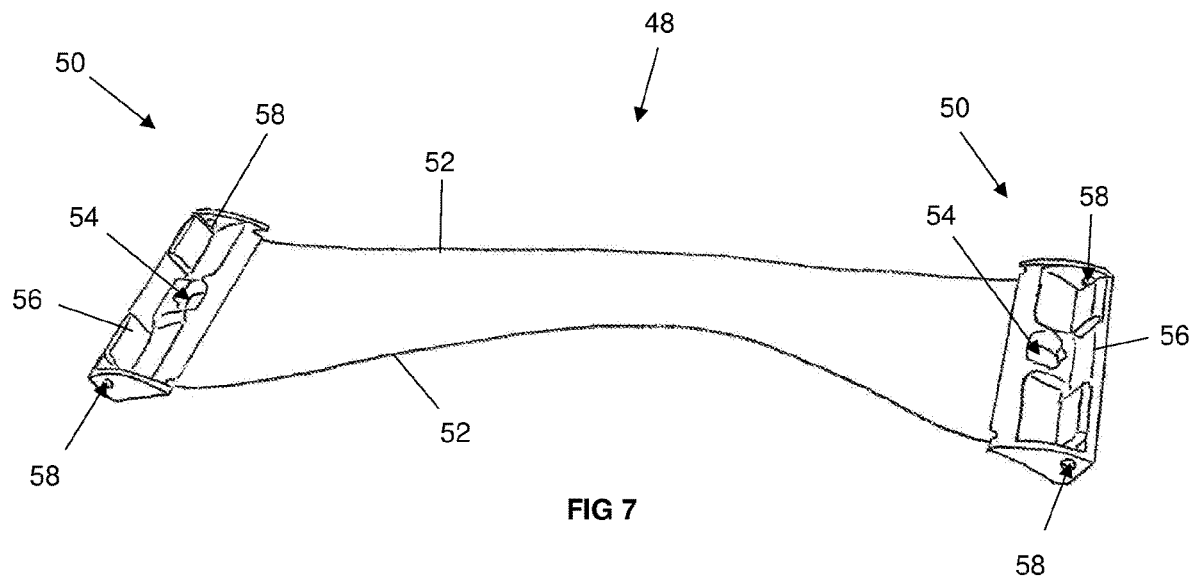
FIG. 7 shows a three-dimensional view of a an attachment assembly according to the present invention, for the goggles of FIG. 1.

Referring to FIG. 7, the goggles 12 includes an attachment assembly 48, which comprises a pair of anchor formations 50, with two resilient tensile elements in the form of thin polymeric wires 52 extending between them. Each of the anchor formations 50 defines a recess or aperture 54 into which the end of one of the tabs 30 is receivable.

Each of the anchor formations 50 includes an outer wall 56 that extends partly around top and bottom ends of the anchor formation and two recesses 58 or apertures are defined in the outer wall at the top and bottom ends.

In the illustrated embodiment, the anchor formations 50 are only visible when they are separate from the roll holder bodies 42, except in FIG. 9 (see below), however, the anchor formations are complemental to the recesses 47 and when they are received in the recesses, they are held in position by clipping engagement of the clips 43 into the recesses 58, so that the outer wall 56 forms part of the outer shell of the roll holder bodies. In other embodiments, the anchor formations 50 can form part of the roll holder bodies 42, permanently.

Figure 8:
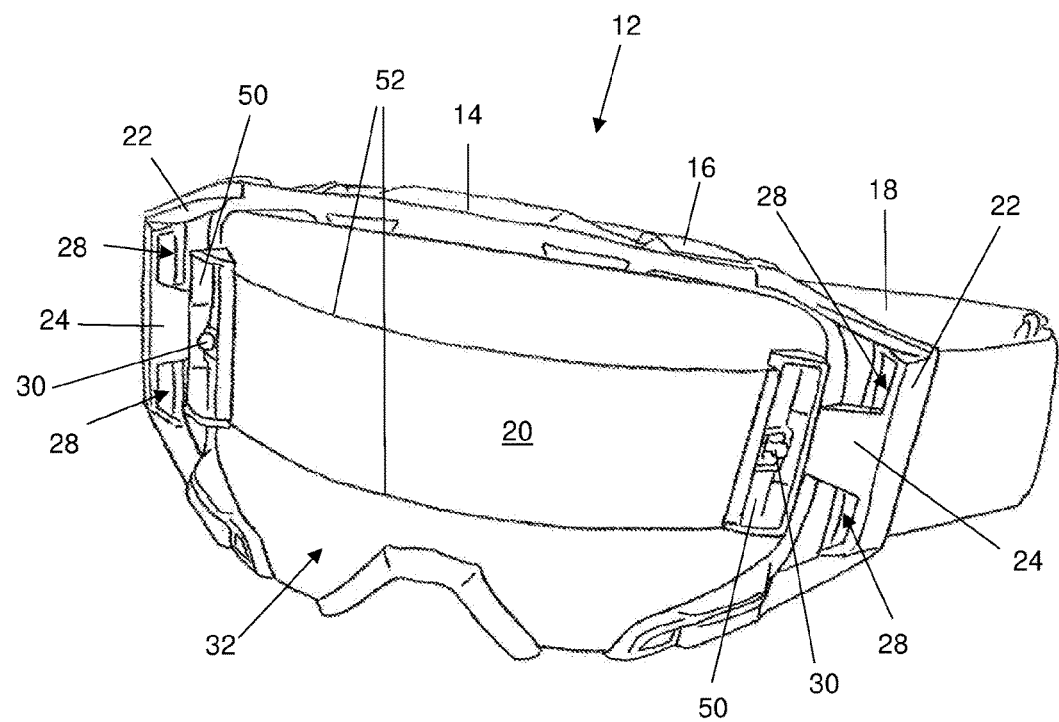
FIG. 8 shows a front perspective view of the goggles of FIG. 1, fitted with the attachment assembly of FIG. 7.
Figure 9:
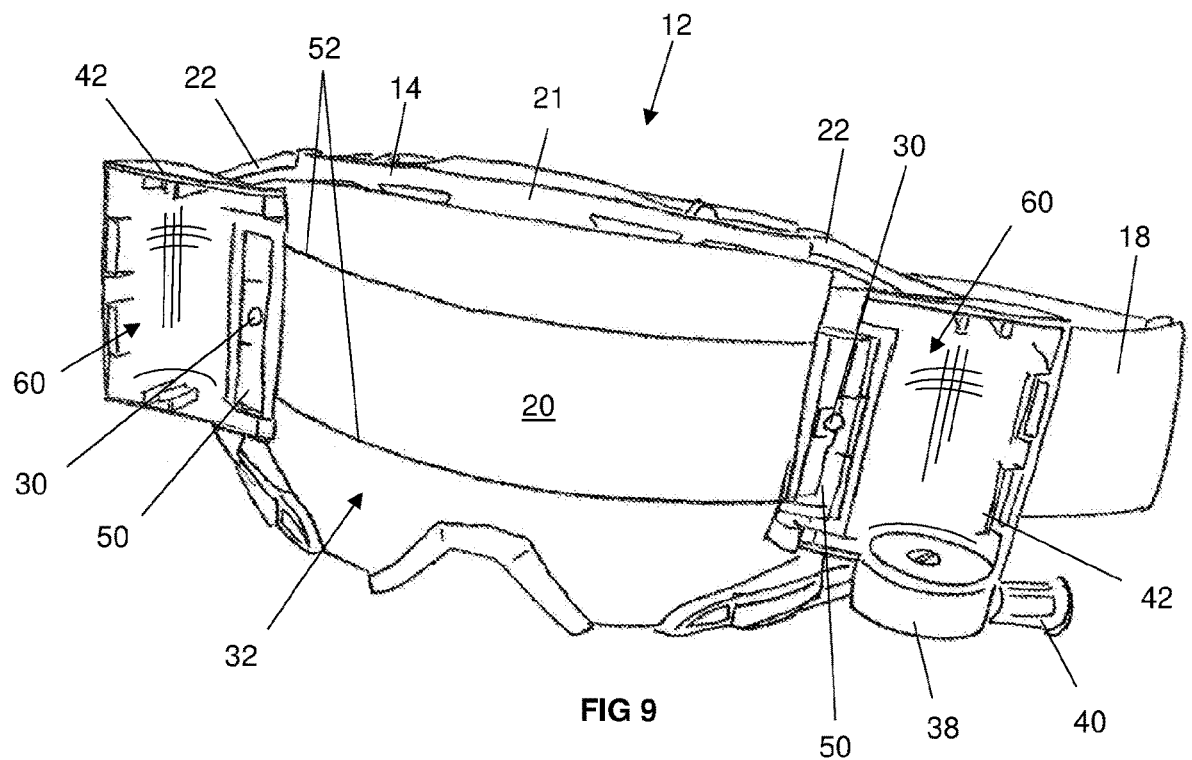
FIG. 9 shows a front perspective view of the goggles of FIG. 8, fitted with roll holders, without front covers of the roll holders.

Referring to FIGS. 8 and 9, if the goggles 12 are to be used with a roll-off system, the roll holders 34,36 can be installed on the goggles 12 by installing each of the anchor formations 50 on one of the tabs 30. The apertures 54 of the anchor formations 50 can be configured so that the anchor formations are held in place on the tabs 30 by a snap fit, friction or the like, but in the illustrated embodiment, the wires 52 are placed under tension and are stretched a little to pass the anchor formations over the tabs and the resilience of the wires causes them to pull the anchor formations towards each other, with peripheral walls of the apertures 54 held nested around the necks of each tab by the tension in the wires.

In the illustrated example, the bodies 42 of the roll holders 34,36 are installed by inserting their tongues 46 into the recesses 28 on the outriggers 22 and pressing the bodies towards the anchor formations 50, so that the anchor formations are received in the recesses 47 and the clips 43 engage with the recesses 58, and so that the outer wall 56 of each anchor formation is contiguous with the shell of its associated roll holder body 42.

In a preferred method of installing the roll holders 34,36 on the goggles 12, the anchor formations 50 are attached to the roll holder bodies 42 first (by clipping them into the recesses 47 and engaging the clips 43 and recesses 58) and each roll holder is attached to the goggles as an assembled unit, by inserting the tongues 46 in the recesses 28 and receiving the tabs 30 in the apertures 54. If desired, the roll holder bodies 42 can be removed from their anchor formations 50.

The roll holder bodies 42 can be attached to the outriggers 22 while the outriggers are in their operative positions, with the clips 26 engaged with the frame body 21, as shown, or preferably, the outriggers can be pivoted forward (with the clips 26 disengaged) before the roll holder bodies are attached to the outriggers and the outriggers and bodies 42 can be pivoted back, together, to engage the clips 26 and to receive the anchor formations 50 in the recesses 47 and to engage the clips 43 in the recesses 58.

Similarly, in embodiments where the anchor formations 50 are fixed to the roll holder bodies 42, either by inserting the anchor formations in the recesses 47 before installing the bodies 42, or in embodiments where the anchor formations are integrally formed with the roll holder bodies, the roll holder bodies are preferably attached to the outriggers 22 while the outriggers are pivoted forwards and the roll holder bodies are attached to the tabs 30 by pivoting the outriggers back, with the roll holder bodies on them, to receive the tabs 30 in the apertures 54 at the same time as re-engaging the clips 26.

Each roll holder body 42 is now held firmly in position relative to the lens 20 and the frame 14, by the attachment of the tongues 46 in the recesses 28 and the attachment of the anchor formations 50 (which now form part of the roll holder bodies) to the tabs 30. The attachment of the roll holder bodies 42 to the frame 14 and lens 20 is secure, at least partly because part of each body 42 is held captive between its associated outrigger 22 and its associated tab 30.

A feed reel, transparent film and take-up reel of a conventional roll-off system can now be installed in the inner cavities 60 of the roll holder bodies 42 in the conventional manner and each roll holder 34,36 can be closed up with its cover 44, so that the roll-off system is ready for use.

While the roll holders 34,36 are installed on the goggles 12, each of them can pivot along with its associated outrigger, relative to the frame body 21, e.g. if the outriggers need to be pivoted to release the lateral edges of the lens 20 from the lock formations 24, to change the lens. In these circumstances, each anchor formation 50 will remain in position on its tab 30, while the roll holder body 42 (and the rest of the roll holder) pivots along with the outrigger (with its tongues 46 still engaged in the recesses 28). The holder body 42 disengages from its anchor formation 50 by clipping disengagement of the clips 43 and recesses 58 so that the roll holder body 42 can pivot along with the outrigger and the clips and recesses 58 re-engage again when the outrigger is pivoted back to its operational position (with its clip 26 engaged with the frame body 21).

While the roll-off system is in use, the transparent film is reeled from time to time from the feed reel in the feed roll holder 34 to the take-up reel in the take-up roll holder 36 and in between these two reels, the film passes over the front surface 32 of the lens 20. The wires 52 extend between the film and the front surface 32 and ensures that the film does not adhere to the lens surface and can slide along easily.

If the roll-off system is no longer needed and/or the wearer wishes to use the tear off system, the roll holders 34,36 are removed by reversing the installation process described above, to disengage each roll holder body 42 from its anchor formation 50 and withdraw the tongues 46 from the recesses 28.

In other embodiments, the attachment assembly could include different tensile elements between the anchor formations 50, or the tensile elements could be omitted and the anchor formations 50 could be integrally formed with the bodies 42 of the roll holders 34,36. If the anchor formations 50 are integrally formed with the roll holder bodies 42, then the anchor formations would pivot along with the rest of the bodies 42 and outriggers 22 and the tabs 30 would still be received in the apertures 54 in the anchor formations. However, the anchor formations 50 would disengage from the tabs 30 when they are pivoted along with the outriggers 22, and they would reengage with the tabs, when the outriggers are returned to their operational positions.

The invention claimed is:

1. A protective eyewear comprising a frame and a lens, said frame comprising a frame body and opposing lateral portions that hold the lens in position on the frame body, said protective eyewear further comprising:
   a pair of engagement features disposed at opposing lateral positions on a front surface of the lens, each of said engagement features protruding from the front of the lens and being shaped and dimensioned for receipt of tear off sheets; and
   a removable pair of roll canisters;
   characterised in that the frame includes first attachment formations disposed at opposing lateral locations on the lateral portions of the frame and each of the roll canisters includes at least one second attachment formation that is complemental to one of the first attachment formations, such that each roll canister is releasably attachable to one of the lateral portions of the frame by engagement of complemental features of one of said first attachment formations on said lateral portion of the frame and one of said second attachment formations on said roll canister, and each of the roll canisters includes an anchor formation defining a recess in which one of the engagement features is receivable; and
   wherein each of the lateral portions of the frame is an outrigger that is pivotally attached to the frame body, the first attachment formations being disposed on each of the outriggers.

2. The protective eyewear according to claim 1, wherein each of the roll canisters includes a body and the anchor formation of each roll canister is releasable from its body.

3. The protective eyewear according to claim 2, wherein each anchor formation is releasably attachable to one of the engagement features and at least part of the body of each roll canister is receivable between the anchor formation and frame.

4. The protective eyewear according to claim 3, wherein said protective eyewear includes an attachment assembly comprising the two anchor formations and at least one resilient tensile element extending between the anchor formations.

5. The protective eyewear according to claim 2, wherein said protective eyewear includes an attachment assembly comprising the two anchor formations and at least one resilient tensile element extending between the anchor formations.

6. The protective eyewear according to claim 1, wherein each of the roll canisters includes a body and the anchor formation of each roll canister is releasable from its body.

7. The protective eyewear according to claim 6, wherein each anchor formation is releasably attachable to one of the engagement features and at least part of the body of each roll canister is receivable between the anchor formation and frame.

8. The protective eyewear according to claim 7, wherein said protective eyewear includes an attachment assembly comprising the two anchor formations and at least one resilient tensile element extending between the anchor formations.

9. The protective eyewear according to claim 6, wherein said protective eyewear includes an attachment assembly comprising the two anchor formations and at least one resilient tensile element extending between the anchor formations.

\* \* \* \* \*